United States Patent
Jackson et al.

(10) Patent No.: US 7,875,677 B2
(45) Date of Patent: Jan. 25, 2011

(54) MICELLAR DRUG DELIVERY SYSTEMS FOR HYDROPHOBIC DRUGS

(75) Inventors: John K. Jackson, Vancouver (CA); Jason Zastre, Vancouver (CA); Helen M. Burt, Vancouver (CA)

(73) Assignee: The University of British Columbia, Vancouver, B.C. (CA)

( * ) Notice: Subject to any disclaimer, the term of this patent is extended or adjusted under 35 U.S.C. 154(b) by 0 days.

(21) Appl. No.: 12/193,648

(22) Filed: Aug. 18, 2008

(65) Prior Publication Data

US 2009/0105351 A1  Apr. 23, 2009

Related U.S. Application Data

(63) Continuation of application No. 11/296,184, filed on Dec. 6, 2005, now abandoned, which is a continuation of application No. 10/475,453, filed as application No. PCT/CA02/00542 on Apr. 22, 2002, now abandoned.

(60) Provisional application No. 60/284,884, filed on Apr. 20, 2001.

(51) Int. Cl.
 *C08L 53/00* (2006.01)
 *C08L 67/00* (2006.01)
 *C08G 63/91* (2006.01)
 *C08G 69/48* (2006.01)
 *A61K 31/74* (2006.01)
 *A61K 38/13* (2006.01)

(52) U.S. Cl. .................... 525/92 B; 525/88; 525/419; 525/420; 528/354; 424/78.17

(58) Field of Classification Search .............. 525/92 B, 525/88, 419, 420; 528/354; 424/78.17
See application file for complete search history.

(56) References Cited

U.S. PATENT DOCUMENTS

| | | | |
|---|---|---|---|
| 4,419,340 A | 12/1983 | Yolles | 424/19 |
| 4,526,938 A | 7/1985 | Churchill et al. | 525/415 |
| 4,650,913 A | 3/1987 | Feiring | 570/144 |
| 4,745,160 A | 5/1988 | Churchill et al. | 525/415 |
| 4,814,470 A | 3/1989 | Colin et al. | 514/449 |
| 4,857,653 A | 8/1989 | Colin et al. | 549/511 |

(Continued)

FOREIGN PATENT DOCUMENTS

CA   2 488 385 A1   12/2003

(Continued)

OTHER PUBLICATIONS

Bishop et al., "Initial Paclitaxel Improves Outcome Compared With CMFP Combination Chemotherapy as Front-Line Therapy in Untreated Metastatic Breast Cancer," *Journal of Clinical Oncology* 17(8):2355-2364, Aug. 1999.

(Continued)

*Primary Examiner*—Duc Truong
(74) *Attorney, Agent, or Firm*—Hai Han; Seed IP Law Group PLLC

(57) ABSTRACT

This invention provides compositions comprising a hydrophobic drug, a biocompatible micelle forming polymer, and a biocompatible low molecular weight, water-soluble polymer. Also provided are devices for injection of such compositions and for the use of such compositions to form hydrophobic drug containing micelles within the body of a patient.

37 Claims, 1 Drawing Sheet

U.S. PATENT DOCUMENTS

| | | | |
|---|---|---|---|
| 4,942,184 A | 7/1990 | Haugwitz et al. | 514/449 |
| 5,059,699 A | 10/1991 | Kingston et al. | 549/511 |
| 5,200,534 A | 4/1993 | Rao | 549/510 |
| 5,202,448 A | 4/1993 | Carver et al. | 549/510 |
| 5,229,529 A | 7/1993 | Ueno et al. | 549/305 |
| 5,248,796 A | 9/1993 | Chen et al. | 549/510 |
| 5,254,580 A | 10/1993 | Chen et al. | 514/449 |
| 5,272,171 A | 12/1993 | Ueda et al. | 514/449 |
| 5,274,137 A | 12/1993 | Nicolaou et al. | 549/510 |
| 5,278,324 A | 1/1994 | Kingston et al. | 549/510 |
| 5,279,949 A | 1/1994 | Nair | 435/123 |
| 5,283,253 A | 2/1994 | Holton et al. | 514/444 |
| 5,294,637 A | 3/1994 | Chen et al. | 514/449 |
| 5,300,638 A | 4/1994 | Farina et al. | 540/357 |
| 5,350,866 A | 9/1994 | Holton et al. | 549/510 |
| 5,352,805 A | 10/1994 | Kingston et al. | 549/510 |
| 5,362,831 A | 11/1994 | Mongelli et al. | 526/304 |
| 5,380,751 A | 1/1995 | Chen et al. | 514/449 |
| 5,393,895 A | 2/1995 | Gaullier et al. | 549/510 |
| 5,393,896 A | 2/1995 | Margraff | 549/510 |
| 5,395,850 A | 3/1995 | Roth | 514/471 |
| 5,411,984 A | 5/1995 | Kingston et al. | 514/449 |
| 5,412,092 A | 5/1995 | Rey et al. | 540/200 |
| 5,422,364 A | 6/1995 | Nicolaou et al. | 514/449 |
| 5,430,021 A | 7/1995 | Rudnic et al. | 514/14 |
| 5,440,056 A | 8/1995 | Klein et al. | 549/510 |
| 5,453,521 A | 9/1995 | Gaullier et al. | 549/541 |
| 5,478,860 A | 12/1995 | Wheeler et al. | 514/449 |
| 5,484,809 A | 1/1996 | Hostetler et al. | 514/449 |
| 5,510,103 A | 4/1996 | Yokoyama et al. | 424/78.08 |
| 5,543,158 A | 8/1996 | Gref et al. | 424/501 |
| 5,645,856 A | 7/1997 | Lacy et al. | 424/455 |
| 5,716,981 A | 2/1998 | Hunter et al. | 514/449 |
| 5,717,103 A | 2/1998 | Denis et al. | 548/215 |
| 5,736,366 A | 4/1998 | Margraff | 435/123 |
| 5,776,486 A | 7/1998 | Castor et al. | 424/450 |
| 5,811,447 A | 9/1998 | Kunz et al. | 514/411 |
| 5,827,533 A | 10/1998 | Needham | 424/450 |
| 5,827,541 A | 10/1998 | Yarwood et al. | 424/489 |
| 5,834,019 A | 11/1998 | Gergely et al. | 424/466 |
| 5,843,891 A | 12/1998 | Sherman | 514/11 |
| 5,886,026 A | 3/1999 | Hunter et al. | 514/449 |
| 5,916,596 A | 6/1999 | Desai et al. | 424/489 |
| 5,939,454 A | 8/1999 | Schwalge et al. | 514/491 |
| 5,955,509 A | 9/1999 | Webber et al. | 514/772.7 |
| 5,968,972 A | 10/1999 | Broder et al. | 514/449 |
| 5,977,375 A | 11/1999 | Denis et al. | 548/215 |
| 5,981,568 A | 11/1999 | Kunz et al. | 514/411 |
| 5,994,341 A | 11/1999 | Hunter et al. | 514/210 |
| 6,004,573 A | 12/1999 | Rathi et al. | 424/426 |
| 6,017,948 A | 1/2000 | Rubinfeld et al. | 514/449 |
| 6,040,330 A | 3/2000 | Hausheer et al. | 514/408 |
| 6,107,332 A | 8/2000 | Ali et al. | 514/449 |
| 6,117,949 A | 9/2000 | Rathi et al. | 525/415 |
| 6,136,846 A | 10/2000 | Rubinfeld et al. | 514/449 |
| 6,153,193 A | 11/2000 | Kabanov et al. | 424/184.1 |
| 6,210,717 B1 | 4/2001 | Choi et al. | 424/501 |
| 6,231,600 B1 | 5/2001 | Zhong | 623/1.42 |
| 6,306,421 B1 | 10/2001 | Kunz et al. | 424/423 |
| 6,322,805 B1 | 11/2001 | Kim et al. | 424/426 |
| 6,358,989 B1 | 3/2002 | Kunz et al. | 514/411 |
| 6,365,173 B1 | 4/2002 | Domb et al. | 424/426 |
| 6,369,037 B1 | 4/2002 | Kim et al. | 514/34 |
| 6,495,579 B1 | 12/2002 | Hunter | 514/365 |
| 6,506,411 B2 | 1/2003 | Hunter et al. | 424/501 |
| 6,515,016 B2 | 2/2003 | Hunter | 514/449 |
| 6,544,544 B2 | 4/2003 | Hunter et al. | 424/424 |
| 6,592,899 B2 | 7/2003 | Fowers et al. | 424/486 |
| 6,616,941 B1 | 9/2003 | Seo et al. | 424/450 |
| 6,689,803 B2 | 2/2004 | Hunter | 514/365 |

FOREIGN PATENT DOCUMENTS

| | | |
|---|---|---|
| CA | 2 490 007 A1 | 1/2004 |
| EP | 1 070 502 A2 | 1/2001 |
| EP | 0 720 471 B1 | 4/2001 |
| EP | 1 092 433 A2 | 4/2001 |
| EP | 0 941 089 B1 | 5/2001 |
| EP | 1 127 570 A2 | 8/2001 |
| EP | 0 590 267 B1 | 5/2002 |
| EP | 0 706 376 B2 | 8/2007 |
| WO | 93/10076 | 5/1993 |
| WO | WO 93/23555 | 11/1993 |
| WO | 93/24476 | 12/1993 |
| WO | 94/00156 | 1/1994 |
| WO | 94/07880 | 4/1994 |
| WO | 94/20089 | 9/1994 |
| WO | 95/03036 | 2/1995 |
| WO | 97/10849 | 3/1997 |
| WO | 97/27855 | 8/1997 |
| WO | 97/40823 | 11/1997 |
| WO | 98/07434 | 2/1998 |
| WO | 98/24427 | 6/1998 |
| WO | 99/21908 | 5/1999 |
| WO | 99/32151 | 7/1999 |
| WO | 99/43343 | 9/1999 |
| WO | 99/62510 | 12/1999 |
| WO | 01/05379 A1 | 1/2001 |
| WO | 01/12718 A1 | 2/2001 |
| WO | 01/30319 A1 | 5/2001 |
| WO | 01/45742 A1 | 6/2001 |
| WO | 01/85216 A1 | 11/2001 |
| WO | 01/87345 A1 | 11/2001 |
| WO | 02/072150 A2 | 9/2002 |
| WO | WO 02/087563 | 11/2002 |
| WO | 03/041689 A1 | 5/2003 |
| WO | 2004/011275 A1 | 2/2004 |

OTHER PUBLICATIONS

Burt et al., "Development of copolymers of poly(D,L-lactide) and methoxypolyethylene glycol as micellar carriers of paclitaxel," *Colloids and Surfaces B: Biointerfaces* 16(1):161-171, Nov. 1999.

Dordunoo et al., "Taxol encapsulation in poly(ε-caprolactone) microspheres," *Cancer Chemother. Pharmacol.* 36(4):279-282, 1995.

Gao et al., "A Model of Micellization for Block Copolymers in Solutions," *Macromolecules* 26(26):7353-7360, 1993.

Georg et al., "Synthesis of Biologically Active Taxol Analogues with Modified Phenylisoserine Side Chains," *J. Med. Chem.* 35(22):4230-4237, 1992.

Gimon et al., "Matrix-Assisted Laser Desorption/Ionization Time-of-Flight Mass Spectrometry of Paclitaxel and Related Taxanes," *Journal of Natural Products*, 57(10):1404-1410, Oct. 1994.

Guéritte-Voegelein et al., "Relationships between the Structure of Taxol Analogues and Their Antimitotic Activity," *J. Med. Chem.* 34(3):992-998, Mar. 1991.

Ha et al., "Poly(ethylene oxide)-poly(propylene oxide)-poly(ethylene oxide) (Pluronic)/poly(ε-caprolactone) (PCL) amphiphilic block copolymeric nanospheres I. Preparation and characterization," *Journal of Controlled Release* 62(3):381-392, 1999.

Hamad et al., "Theory of Micelle Formation by Amphiphilic Side-Chain Polymers," *Macromolecules*, 23(19):4185-4191, Sep. 17, 1990.

Holton et al., "A Synthesis of Taxusin," *J. Am. Chem. Soc.* 110(19):6558-6560, Sep. 14, 1988.

Inoue et al., "An AB block copolymer of oligo(methyl methacrylate) and poly(acrylic acid) for micellar delivery of hydrophobic drugs," *Journal of Controlled Release* 51(2):221-229, Feb. 12, 1998.

Jackson et al., "A polymer-based drug delivery system for the antineoplastic agent bis(maltolato)oxovanadium in mice," *British Journal of Cancer* 75(7):1014-1020, 1997.

Jackson et al., "The Suppression of Human Prostate Tumor Growth in Mice by the Intratumoral Injection of a Slow-Release Polymeric Paste Formulation of Paclitaxel," *Cancer Research* 60(15):4146-4151, Aug. 1, 2000.

Kataoka et al., "Doxorubicin-loaded poly(ethylene glycol)-poly(β-benzyl-L-aspartate) copolymer micelles: their pharmaceutical characteristics and biological significance," *Journal of Controlled Release* 64(1-3):143-153, Feb. 2000.

Kim et al., "Methoxy poly(ethylene glycol) and ε-caprolactone amphiphilic block copolymeric micelle containing indomethacin. II. Micelle formation and drug release behaviours," *Journal of Controlled Release* 51:13-22, 1998.

Kim et al., "Amphiphilic diblock copolymeric nanospheres composed of methoxy poly(ethylene glycol) and glycolide: properties, cytotoxicity and drug release behaviour," *Biomaterials* 20(11):1033-1042, 1999.

Kim et al., "Poly(ethylene oxide)-poly(propylene oxide)-poly(ethylene oxide)/poly(ε-caprolactone) (PCL) amphiphilic block copolymeric nanospheres II. Thermo-responsive drug release behaviors," *Journal of Controlled Release* 65(3):345-358, Apr. 3, 2000.

Kim et al., "In vivo evaluation of polymeric micellar paclitaxel formulation: toxicity and efficacy," *Journal of Controlled Release* 72(1-3):191-202, 2001.

Kim et al., "Indomethacin-loaded methoxy poly(ethylene glycol)/poly(ε-caprolactone) diblock copolymeric nanosphere: pharmacokinetic characteristics of indomethacin in the normal Sprague-Dawley rats," *Biomaterials* 22(14):2049-2056, 2001.

Kim et al., "Taxol-loaded block copolymer nanospheres composed of methoxy poly(ethylene glycol) and poly(ε-caprolactone) as novel anticancer drug carriers," *Biomaterials* 22(13):1697-1704, Jul. 2001.

Kreuter, J., "Nanoparticle-based drug delivery systems," *Journal of Controlled Release* 16(1-2):169-176, Jun.-Jul. 1991.

Kwon et al., "Polymeric micelles as new drug carriers," *Advanced Drug Delivery Reviews* 21(2):107-116, Sep. 16, 1996.

La et al., "Preparation and Characterization of the Micelle-Forming Polymeric Drug Indomethacin-Incorporated Poly(ethylene oxide)-Poly(β-benzyl L-aspartate) Block Copolymer Micelles," *Journal of Pharmaceutical Sciences* 85(1):85-90, Jan. 1996.

Lemoine et al., Stability study of nanoparticles of poly(ε-caprolactone), poly(D, L-lactide) and poly(D,L-lactide-co-glycolide), *Biomaterials* 17(22):2191-2197, 1996.

Long et al., "Paclitaxel Inhibits Progression of Mitotic Cells to G1 Phase Interference with Spindle Formation without Affecting Other Microtubule Functions during Anaphase and Telephase," *Cancer Research* 54(16):4355-4361, Aug. 15, 1994.

Malmsten et al., "Self-Assembly in Aqueous Block Copolymer Solutions," *Macromolecules* 25(20):5440-5445, 1992.

Marchal-Heussler et al., "Poly(ε-Caprolactone) Nanocapsules in Carteolol Ophthalmic Delivery," *Pharmaceutical Research* 10(3):386-390, Mar. 1993.

Martin et al., "Physical Pharmacy: Physical Chemical Principles in the Pharmaceutical Sciences," 4th Edition, *Lippincott Williams & Wilkins*, Philadelphia, PA, 1993.

Munk et al., "Characterization of Block Copolymer Micelles in Aqueous Media," *Journal of Applied Polymer Science: Applied Polymer Symposium* 52:45-54, 1993.

Nicoletti et al., "IDN5109, a Taxane with Oral Bioavailability and Potent Antitumor Activity," *Cancer Research* 60(4):842-846, Feb. 15, 2000.

Pazdur et al., "The taxoids: paclitaxel (Taxol®) and docetaxel (Taxotere®)," *Cancer Treatment Reviews* 19(4):351-386, Oct. 1993.

Piskin et al., "Novel PDLLA/PEG copolymer micelles as drug carriers," *J. Biomater. Sci. Polymer Edn.* 7(4):359-373, 1995.

Price et al., "Thermodynamics of Micellization of Poly-styrene-*block*-Poly(ethylene/propylene) Copolymers in Decane," *British Polymer Journal* 21(5):391-394, 1989.

Pulicani et al., "Preparation of 7-Modified Docetaxel Analogs Using Electrochemistry," *Tetrahedron Letters*, 35(52):9709-9712, 1994.

Quintana et al., "Micellization of a Polystyrene-*block*-poly(ethylene/propylene) Copolymer in *n*-Alkanes. 1. Thermodynamic Study," *Macromolecules* 25(12):3125-3128, 1992.

Ringel et al., "Studies With RP 56976 (Taxotere): A Semisynthetic Analogue of Taxol," *Journal of the National Cancer Institute* 83(4):288-291, Feb. 20, 1991.

Schiff et al., "Promotion of microtubule assembly in vitro by taxol," *Nature* 277:665-667, Feb. 22, 1979.

Seijo et al., "Design of nanoparticles of less than 50 nm diameter: preparation, characterization and drug loading," *International Journal of Pharmaceutics* 62(1):1-7, Jul. 15, 1990.

Shin et al., "Methoxy poly(ethylene glycol)/ε-caprolactone amphiphilic block copolymeric micelle containing indomethacin. I. Preparation and characterization," *Journal of Controlled Release* 51(1):1-11, 1998.

Stierle et al., "Taxol and Taxane Production by *Taxomyces andreanae*, an Endophytic Fungus of Pacific Yew," *Science* 260(5105):214-216, Apr. 9, 1993.

Tanodekaew et al., "Association and surface properties of diblock copolymers of ethylene oxide and DL-lactide in aqueous solution," *Macromol. Chem. Phys.* 198(4):927-944, 1997.

Terwogt et al., "Coadministration of Oral Cyclosporin A Enables Oral Therapy with Paclitaxel," *Clinical Cancer Research* 5(11):3379-3384, Nov. 1999.

van Asperen et al., Enhanced oral bioavailability of paclitaxel in mice treated with the P-glycoprotein blocker SDZ PSC 833, *British Journal of Cancer* 76(9):1181-1183, 1997.

Wani et al., "Plant antitumor agents. VI. The isolation and structure of taxol, a novel antileukemic and antitumor agent from *Taxus brevifolia*," *J. Am. Chem. Soc.* 93(9):2325-2327, May 5, 1971.

Winternitz et al., "Development of a Polymeric Surgical Paste Formulation for Taxol," *Pharmaceutical Research* 13(3):368-375, Mar. 1996.

Yu et al., "In vitro dissociation of antifunal efficacy and toxicity for amphotericin B-loaded poly(ethylene oxide)-block-poly(β-benzyl-L-aspartate) micelles," *Journal of Controlled Release* 56(1-3):285-291, 1998.

Zhang et al., "Yunantaxusin A, A New 11(15-1)-*Abeo*-Taxane From *Taxus Yunnanensis*," *Journal of Natural Products* 57(11):1580-1583, Nov. 1994.

Torchilin, V., "Structure and design of polymeric surfactant-based drug delivery systems," *Journal of Controlled Release* 73:137-172, 2001.

Yokoyama et al., "Incorporation of water-insoluble anticancer drug into polymeric micelles and control of their particle size," *Journal of Controlled Release* 55:219-229, 1998.

Zhang et al., "Development of amphiphilic diblock copolymers as micellar carriers of taxol," *International Journal of Pharmaceutics* 132(1):195-206, Apr. 30, 1996.

MICELLAR DRUG DELIVERY SYSTEMS FOR HYDROPHOBIC DRUGS

This application is a CON of Ser. No. 11/296,184 filed Dec. 6, 2005 now ABN

Which is a CON of Ser. No. 10/475,453 filed May 28, 2004 now ABN

Which is 371 of PCT/CA02/00542 flied Apr. 22, 2002

Which claims benefit of 60/284,884 filed Apr. 20, 2001.

FIELD OF THE INVENTION

This invention relates to micellar compositions for drug formulation and drug delivery.

BACKGROUND OF THE INVENTION

There are a large number of therapeutic compounds that, due to poor water solubility, will not dissolve well in aqueous pharmaceutical carriers (making administration difficult) and exhibit poor availability. One solution has been to reformulate such drugs as water-soluble derivatives. This approach often yields compounds with less efficacy that the parent compound.

Another solution has been to incorporate hydrophobic drugs into micelles. Such micellar formulations are expected to achieve some level of circulation concentration of the drug without precipitation of the drug in the bloodstream. The principle behind micelle formation is that amphipathic molecules can form aggregates in an aqueous environment whereby hydrophobic components of the molecules come together to exclude water and make up the inner core of the micelle. The hydrophilic components of the molecules are orientated towards the outside of the micelle. This aggregation occurs above the critical micelle concentration (CMC) of the molecules in water. Under careful conditions, hydrophobic drugs may be solubilized in the inner hydrophobic core of micelles during their formation. These micellar formulations are utilized almost exclusively for the systemic administration of drugs and are usually delivered intravenously or intraperitoneally, but have also been suggested for oral administration.

The literature describes numerous methods to incorporate hydrophobic drugs such as methotrexate, indomethacin, paclitaxel and doxorubicin into micelles made from biocompatible, amphipathic polymeric molecules (e.g. U.S. Pat. No. 6,322,805; Kim S Y et al. J. Controlled Release (1998) 56:13-22; Inoue T et al. J. Controlled Release (1998) 51:221; and, Kataoka K I J Controlled Release (2000) 64:143-153). While the literature does describe formation of hydrophobic drug containing micelles with the hydrophobic drug and a micelle forming polymer being in aqueous solution during vigorous agitation or sonication of the solution, the amount of drug loading is poor as a result of its low solubility. Thus, micellar compositions are typically made by dissolving a hydrophobic drug in a water miscible organic solvent in which the drug is soluble, combining the resulting solution with a micellar composition in an aqueous solution with mixing by vigorous stirring, agitation, or sonication. For example, the mixture might be stirred for up to about 24 hours and any remaining drug not incorporated into micelles then removed. The resulting micellar solution may then be used directly for administration or freeze-dried into nanoparticles (which may be resuspended in water at a later time) providing the solvent is biocompatible and/or is capable of being removed by freeze-drying or other methods. These methods are complicated, expensive, and expose potentially water labile drugs to long periods in aqueous media. In addition there is a need to remove the organic solvent, which is often not pharmaceutically compatible or desirable.

One process for removal of an organic solvent is by solvent evaporation. In this method, a hydrophobic drug is typically dissolved in a water-miscible organic solvent and introduced to an aqueous solution of micelles. Subsequently, the organic solvent is evaporated off at elevated temperature. Alternatively, the drug and a micelle forming polymer are both dissolved in an organic solvent and the solvent is evaporated at elevated temperature. The resulting mixture is kept at an elevated temperature while warm water or aqueous solution is added with vigorous stirring until polymeric micelles containing the drug are formed. Also a dialysis method can be used, where a suitable water-miscible organic solvent is used to dissolve the hydrophobic drug and the micelle forming polymer. The solution is subsequently dialysed against a buffer solution and then against water. In some cases the duration of dialysis may be as long as 72 hours (Yu B. G. et al. J Controlled Release (1998) 56:285-291).

U.S. Pat. No. 4,745,160 (Churchill J. R. et al.) teaches a process for manufacturing micelle compositions from biodegradable amphipathic copolymers. The patent teaches that in order to incorporate a hydrophobic drug it is necessary to dissolve the drug in a water miscible organic solvent such as dioxan, acetic acid, acetonitrile, methanol or ethanol.

U.S. Pat. No. 5,510,103 (Yokoyama M. et al.) and U.S. Pat. No. 5,939,453 (Heller J. et al.) describe micelles made of block copolymers in which hydrophobic drugs are physically trapped. However, the disclosed methods of trapping require beating, ultrasonication, and/or the use of organic solvents and dialysis.

U.S. Pat. No. 6,136,846 (Rubinfeld J. et al.) describes incorporation of paclitaxel into micelles made from amphipathic block copolymers in which the hydrophobic block is a lipid tail. Organic solvents are used but the patent also teaches that polyethylene glycol (PEG) of 300-400 molecular weight may be used as the "solubilizer". Paclitaxel loading of about 2% is reported in the examples set out in the patent.

Zhang X. et al. (Int'l. J. Pharmaceutics (1996) 132:195-206) reports the formation of a matrix containing taxol and a diblock copolymer composed of methoxy polyethylene glycol (MePEG) and polylactic acid. Only if the matrix is made with acetonitrile as an organic solvent, will the resulting matrix be capable of forming micelles following evaporation of the solvent. The resulting matrix must be heated to melt the polymer and vigorously agitated in aqueous medium in order to produce drug containing micelles.

In WO9921908, Zhang, X. et al., teaches the production of a semi-solid polymer mixture comprising hydrophobic drug, a water soluble polymer such as MePEG, and a hydrophobic polymer. It was found that the hydrophobic drug precipitates in the mixture thereby solidifying the material:

SUMMARY OF THE INVENTION

This invention provides micellar compositions for improved hydrophobic drug loading and compositions comprising hydrophobic drugs capable of forming drug containing micelles which may be made without a non-polymeric organic solvent and without heating or agitation. This invention allows for the formulation and non-oral administration by injection of semi-solid mixtures into the body of a patient whereby the semi-solid material spontaneously forms micelles containing the hydrophobic drug which enter the bloodstream.

In one aspect, the present invention provides for improved hydrophobic drug loading into micelles by using selected amphipathic diblock copolymers including those described by Zhang et al. (1996), without an organic solvent such as acetonitrile being required. The micelles are formed from a micelle forming composition comprising a biocompatible, low molecular weight, water soluble polymer (including the PEG "solubilizer" taught in U.S. Pat. No. 6,136,846 and the micelle forming compositions of this aspect of the invention exhibit low critical micelle concentrations (CMC) under about 500 µM to as low as about 20 µM as determined by standard techniques). Hydrophobic drug loading using this aspect of the invention can achieve drug levels in the micellar composition in excess of 10% (by weight) and as high as about 25% when the CMC is about 50 µM or less. This is surprising because Zhang et al. (1996) found such diblock copolymer formulations required acetonitrile to adequately distribute taxol in a matrix in order for micelles to be produced from the matrix. WO9921908 suggests that making a polymeric composition comprising a free water soluble polymer and a hydrophobic drug will result in precipitation of the drug, which is counter-productive to the production of micelles. Further, Zhang et al. (1996) suggests that increasing amounts of a water soluble polymer (MePEG) in a matrix results in less efficient micelle production from the matrix and poor distribution of the drug in the matrix.

This aspect of the invention provides a micelle forming composition comprising:
(a) one or more hydrophobic drugs;
(b) one or more biocompatible, micelle forming polymers; and,
(c) one or more biocompatible, low molecular weight, water soluble polymers, wherein the micelle forming polymer is a copolymer comprising a hydrophobic and a hydrophilic portion, the hydrophobic portion being selected from the group consisting of: a polyester and a polyanhydride; and, the hydrophilic portion is a polyethylene oxide having a molecular weight of about 750 or more. Also provided are micelles formed from the aforementioned composition.

A second aspect of the invention results from the discovery that a micellar composition comprising a biocompatible micelle forming polymer, a biocompatible, low molecular weight water soluble polymer; and, a hydrophobic drug, may be formulated as a semi-solid material (e.g. a wax like substance or a paste) capable of being injected into a patient and which will spontaneously form drug containing micelles at the site of deposition of the material in the patient. The water soluble polymer may be one that is liquid or semi-solid at about room temperature (e.g. at about 20-30° C.). Once the material has been injected into a patient or is simply placed in an aqueous solution, it will form hydrophobic drug containing micelles without the need for heating or agitation. This aspect of the invention has the advantage of providing short to medium term localization of a drug at a specific site of injection in a patient, with the drug being released inside micelles to the physiological environment of the site and ultimately to the bloodstream. This aspect of the invention includes compositions comprising a hydrophobic drug, a biocompatible micelle forming polymer and a sufficient amount of a biocompatible low molecular weight water soluble polymer such that the composition is a semi-solid (e.g. a "paste") at temperatures at or about room temperature and is injectable through a syringe.

This aspect of the invention provides a micelle forming composition comprising:
(a) one or more hydrophobic drugs;
(b) one or more biocompatible, micelle forming polymers; and,
(c) one or more biocompatible, low molecular weight, water soluble polymers, wherein the one or more water soluble polymers are present in an amount sufficient that the composition is injectable.

This invention also provides methods for using the aforementioned compositions to form micelles in vitro and in vivo. In vivo methodologies include injection of the composition to a site in a patient's body where drug containing micelles are formed at the site.

This invention also provides injection devices such as a syringe containing a micelle forming composition according to this invention.

DETAILED DESCRIPTION OF THE INVENTION

Figure 1:
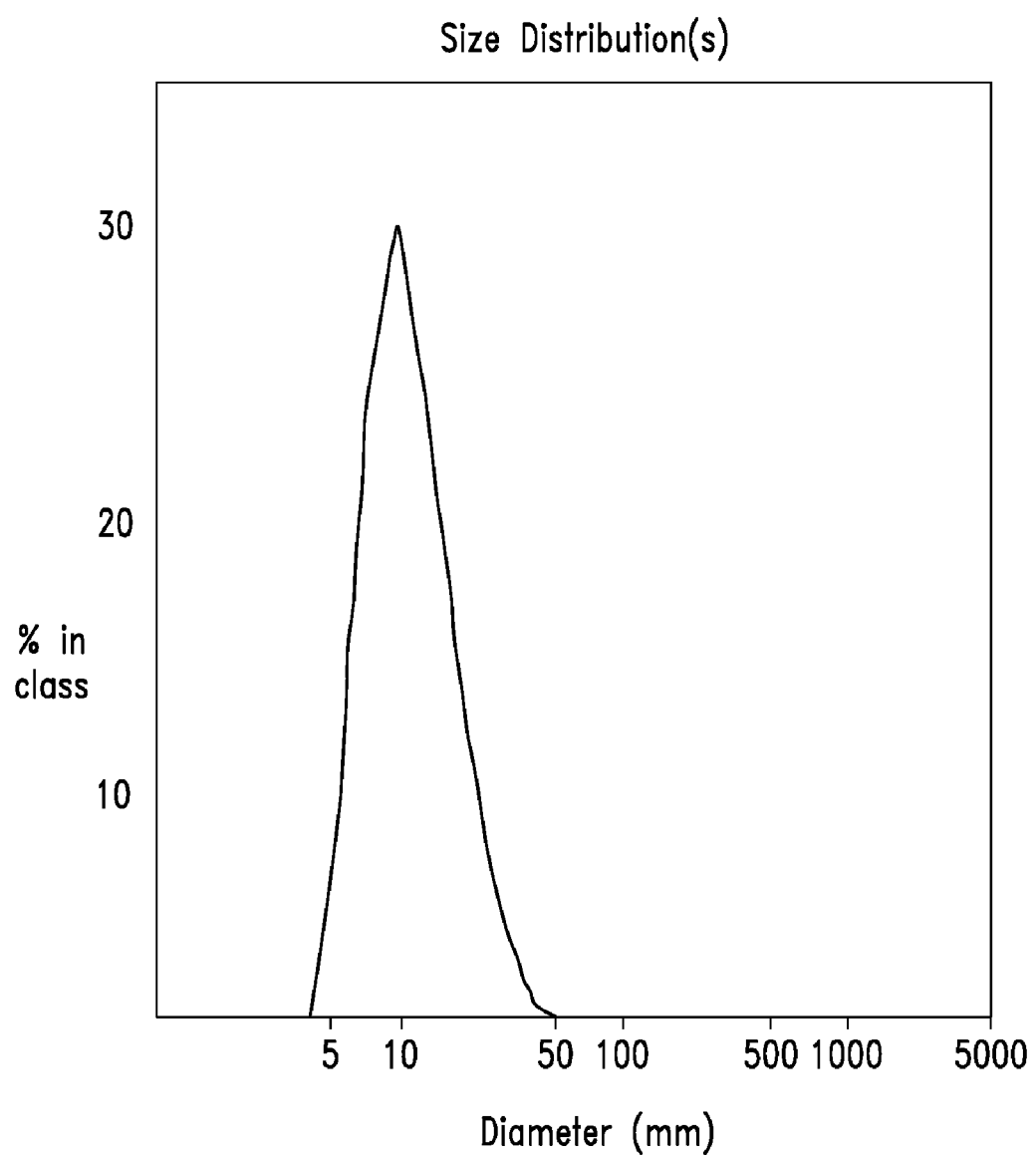
FIG. 1 is a graph showing size distribution micelles with a peak at a particle size diameter of approximately 10 nm. Size distribution was measured on a Zetasizer 3000HS at a temperature of 25 C., at a count rate of 12.0 kCps, with a detector angle of 90.00 and at a wavelength of 633.0.

In the description that follows, a number of terms are used extensively, the following definitions are provided to facilitate understanding of the invention.

"Micelle forming polymer" as used herein refers to an amphipathic polymer that is comprised of both a hydrophilic and a hydrophobic component and which is capable of forming micelles in water. Numerous examples are known and are disclosed in the art Micelle forming polymers include block (e.g. diblock) copolymers comprising a hydrophobic block and a hydrophilic block such as are disclosed in the prior art documents referred to above and in WO01/87345. The micelle forming polymers known in the art that are employed in this invention are those that are biocompatible and thus pharmaceutically suitable. Such is the case for the specific polymers disclosed herein.

As used herein, a "hydrophobic drug," is a water insoluble drug. A "drug" is a therapeutically active substance which is delivered to a living subject to produce a desired effect, such as to treat a condition of the subject. A drug is also provided to a subject prophylactically to prevent the development of a condition or to decrease the severity of a condition that the subject may develop. A "water insoluble drug" has a solubility of less than 0.1 mg/mL in distilled water at 250 C. Within the context of the present invention, a "slightly soluble drug" (solubility: 1-10 mg/mL) and a "very slightly soluble drug" (solubility: 0.1-1 mg/mL) may also be referred to. These terms are well-known to those of skill in the art. See, e.g., Martin (ed.), Physical Pharmacy, Fourth Edition, page 213 (Lea and Febiger 1993). Examples of hydrophobic drugs include the following agents including their water soluble derivatives and analogs:

(a) Amphotericin: used for the treatment or prevention of infection of an open wound by topical administration or for the treatment or prevention of an infection in an exposed wound after surgery by local application. Amphotericin is an antifungal and is insoluble in water at pH 6 to 7 (The Merck Index.).

(b) Anthralin: used for the treatment of "wet" psoriasis by topical application. Anthralin is an agent for psoriasis therapy and is practically insoluble in water (The Merck Index).

(c) Beclomethasone: used for the reduction of local inflammation by peri-ophthalmic and inside the eyelid or intranasal (e.g., for the treatment of rhinitis) application. Beclomethasone is a corticosteroid and is very slightly soluble in water. See, for example, Gennaro, (ed.), Remington's Pharmaceutical Sciences. 17th Edition, (Mack Publishing Company 1985).

(d) Betamethasone: used for the reduction of local inflammation by oral (e.g., canker sore), intravaginal, and intrarectal application. Betamethasone is a corticosteroid and has a solubility of 190 µg/mL water. See, for example, Gennaro, (ed.), Remington's Pharmaceutical Sciences, 17th Edition, (Mack Publishing Company 1985).

(e) Camptothecin: used for the treatment of diseases involving cellular proliferation such as cancer, arthritis, psoriasis, restenosis, surgical adhesions. Camptothecin has a water solubility of 1-2 µg/mL.

(f) Curcumin: a potent antioxidant and potential antiarthritic drug. Curcumin is practically insoluble in water.

(g) Dexamethasone: used for the reduction of local inflammation by oral application (e.g., post wisdom tooth removal). Dexamethasone is a corticosteroid and has a solubility of 10 µg/mL in water (The Merck Index).

(h) Genistein: a tyrosine kinase inhibitor and potentially used for the treatment of diseases involving cellular proliferation. Genistein is practically insoluble in water.

(i) Indomethacin: used for the treatment of symptoms of gout by intraarticular or intramuscular injection or for the reduction of local inflammation by peri-ophthalmic and inside the eyelid, oral, intranasal, intravaginal and intrarectal application. Indomethacin is a non-steroidal anti-inflammatory (NSAID) and is practically insoluble in water (The Merck Index).

(j) Lidocaine: provides local anesthesia by intramuscular injection, or administration by application to mucus membranes, including periophthalmic and inside the eyelid, oral, intranasal, intravaginal and intrarectal. Lidocaine is a local anesthetic and is practically insoluble in water. See, for example, Gennaro, (ed.), Remington's Pharmaceutical Sciences, 17th Edition, (Mack Publishing Company 1985).

(k) Taxol (e.g. Paclitaxel): used for the treatment of angiogenic related diseases such as arthritis, cancer, restenosis, psoriasis, or surgical adhesions. Paclitaxel has a water solubility of 1-2, µg/mL.

(l) Tetracycline: used for the treatment of eye infections by periophthalmic and inside the eyelid application. Tetracycline is an antibacterial and has a solubility of 400 pg/mL water. See, e.g., Gennaro, (ed.), Remington 's Pharmaceutical Sciences, 17th Edition, (Mack Publishing Company 1985).

(m) Tretinoin: a retinoic acid that is potentially an anticancer agent. Tretinoin is practically insoluble in water.

(n) Therapeutic proteins: proteins that are practically insoluble in water, such as insulin, are contemplated for use in this presently described polymeric drug delivery system.

The present invention does not require the use of an organic solvent as traditionally used for dissolving a hydrophobic drug during preparation of drug containing micelles. The term "organic solvent" as used herein with reference to this invention means a non-polymeric solvent, such as an aromatic hydrocarbon, ester, ether, ketone, amine, alcohol, nitrated hydrocarbon and chlorinated hydrocarbon, which non-polymeric solvents include: acetone, ethanol, tetrahydrofuran, acetonitrile and pyrrolidones. Some of these organic solvents are not biocompatible and organic solvents are not suitable for injection into various areas of the patients body, particularly the eye, blood vessels, or the synovial joint.

This invention makes use of a biocompatible, low molecular weight, water soluble polymer in place of an organic solvent as defined above. This obviates the need to remove an organic solvent and permits the formation of hydrophobic drug containing micelles without heating, agitation, vigorous stirring or sonication. It also makes possible the preparation of a semi-solid capable of forming micelles in vivo, for administration by injection to a patient.

The term "injectable" as used herein refers to compositions having a viscosity that permits injection of the material into the body of a patient using a syringe and a needle cannula with the amount of pressure required to inject the material being that which may be comfortably exerted through hand pressure. Material having viscosities between about 5 and about 200 poise which may be measured using known techniques (for example with a parallel plate rheometer). Material that is injectable according to this invention is injectable in a typical temperature range for injection. Preferably, the material is injectable from about room temperature to about body temperature. Most preferably, the material is injectable in a temperature range from about 20° C. to about 40° C.

The terms "substantially free of . . . " or "containing substantially no . . . " with reference to a possible ingredient in a composition means that the composition comprises none, or essentially none of the ingredient. By this definition, the ingredient may be present in such small amounts in the composition that do not affect the properties or pharmaceutical utility of the composition.

Micelle forming compositions according to this invention may be prepared using standard techniques whereby the required polymeric ingredients and a hydrophobic drug are thoroughly mixed or intermingled. Mechanical mixing procedures may be employed, such as are taught in the Examples below. The goal is to achieve a thorough blending of the ingredients of the composition.

Injection devices such as syringes may be prepared so as to contain micelle forming compositions of this invention by using any technique whereby the composition is placed within the injection device in a manner that the composition becomes injectable by the device. For example, a composition of this invention may be placed within the barrel of a syringe by mechanical means or extrusion.

Compositions of this invention may be stored for substantial lengths of time. When a hydrophobic drug is present in a composition of this invention, it is preferred that the composition be stored at a temperature below that of room temperature in accordance with the stability parameters of the selected drug.

Compositions of this invention may be placed in sterile containers for subsequent pharmaceutical formulation. Such a container may be a sealed vial which preferably will contain sufficient space for the subsequent addition of an aqueous, physiologically acceptable carrier. Thus, the compositions of this invention may be employed for production of drug containing micelles within the aforementioned container after introduction of the aqueous carrier. Dissolution of the composition in the carrier with concomitant formation of drug containing micelles may be accelerated by agitation (e.g. shaking) although the compositions of this invention will dissolve over time, without agitation. Long term or vigorous agitation or sonication is not necessary.

Methods for administration of compositions according to this invention and drug containing micellar suspensions made from such compositions may be done according to methods known in the art. Methodologies for injection of such compositions or solutions at a selected site within the body of a patient may be selected and performed by a medical professional.

For injectable compositions of this invention, the composition will comprise one or more biocompatible micelle forming polymers. Such micelle forming polymers may be any such polymer known in the art, including the references referred to above and in WO 01/87345. Preferably, one or more micelle forming polymers in compositions of this invention will be a diblock copolymer suitable for formation of micelles as taught in the art or as specifically described herein. Hydrophobic portions of such diblock copolymers may comprise one or more hydrophobic polymers, such as polyesters, polyanhydrides, polyglycolic acids, polybutrylactones, polyhydroxybutyrates, polylactic acids and polylacaprolactones. The hydrophobic portion of the copolymer may comprise one or more different hydrophobic polymers in random or block orientation. Preferably, the hydrophobic portion of a copolymer will have a molecular weight from about 200 to about 5000.

The preferred micelle forming polymers described above are capable of forming micelles at very low critical micelle concentrations (CMC), which allows for loading of high concentrations of hydrophobic drugs.

Preferred hydrophilic portions of micelle forming copolymers that may be used in this invention have a molecular weight of about 750 or greater up to about 8000. Preferably, the molecular weight will be in the range of about 1000 or 2000-3000 or 5000. Most preferred is a molecular weight of polymer as the hydrophilic portion of the micelle forming polymer being about 2000.

Biocompatible water soluble polymers for use in this invention include any suitable water soluble polymer capable bf fluidizing a micelle forming polymer as used in this invention. Such water soluble polymers include pluronics that is a liquid or solid at room temperature, or low molecular weight polyesters such as glycolitic or lactic acid polymers of sufficiently low molecular weight that the polymer is a liquid or semi-solid at room temperature (e.g. about 20 to 30° C.). Preferred water soluble polymers for use in this invention are polyethylene oxides of a molecular weight of about 1000 or less, including PEG and MePEG.

Weight ratios of hydrophobic and hydrophilic components of micelle forming polymers used in this invention may be adjusted to provide for a desired CMC. The amount of water soluble polymer employed in compositions of this invention may be adjusted to achieve a desired consistency of the resulting mixture of matrix. For injection, it is preferred that the amount of water soluble polymer be such that the resulting mixture or matrix is injectable, as defined herein. The amount of hydrophobic drug included in the composition will be such as to provide a desired amount of drug loaded micelles, preferably not exceeding an amount that can be sufficiently distributed within the micelle forming composition.

Example 1

Manufacture of Diblock Copolymer

Methoxypolyethylene glycol (MePEG) oligomers of molecular weight 750 and 2000 and stannous octoate were obtained from Sigma-Aldrich (St Louis, Mo.), while ϵ-Caprolactone was obtained from Aldrich Milwaukee, Wis.). Chloroform and dichloromethane (DCM) were HPLC grade (Fisher Scientific, Fair Lawn, N.J.).

Copolymers of methoxypolyethylene glycol (MePEG) and poly(ϵ-caprolactone) were prepared as follows. MePEG oligomers with molecular weights of 750 and 2000 were combined with ϵ-caprolactone in varying weight ratios to control the final molecular weight of the copolymer. The total weight of the two reagents was 50 g. The reagents were placed in a round bottom flask sealed with a ground glass stopper and immersed in a heavy mineral oil bath heated to 140° C. The temperature was controlled using a Dyna-Sense MK-1 controller (Scientific Instruments Inc., Skokie, Ill.). The reagents were stirred using a teflon coated 2.5 cm magnetic stir bar. After the reagents were mixed for 30 minutes to produce a homogeneous liquid, 0.15 ml of stannous octoate was added to the flask. The polymerization reaction was allowed to proceed for 6 hours. Cooling the polymer to room temperature terminated the reaction.

Example 2A

Manufacture of A Micellar Formulation of Paclitaxel

Fifty mg of paclitaxel (Hauser chemicals), 380 mg of methoxypolyethylene glycol (MePEG) (molecular weight 350) (Union Carbide Inc.) and 570 mg of poly-L-lactic acid-MePEG diblock copolymer (Angiotech Pharmaceuticals, Vancouver Canada) were weighed into a 20 ml glass vial and stirred at 50° C. using a spatula. The mixture formed a miscible composition in which all the drug was dissolved. The mixture was sucked up into a 1 ml syringe through an 18 gauge needle and allowed to cool to room temperature.

The waxy material could be injected easily through a 21-gauge needle without compromise of the integrity of the composition. When 100 µl of the mixture was injected into 5 ml of water the mixture slowly dissolved. There was no precipitation of any of the components. The formulation self assembled into micelles with a particle size of approximately 10 nm diameter, as shown in FIG. 1. This solution had a paclitaxel concentration of 1 mg/ml, almost 1000 fold greater than the free solubility of the drug in water.

Example 2B

Manufacture of Alternate Micellar Formulation of Paclitaxel

Fifty mg of paclitaxel (Hauser chemicals), 95 mg of methoxypolyethylene glycol (MePEG) (molecular weight 350) (Union Carbide Inc.), 645 mg of poly-L-lactic acid-MePEG diblock copolymer (Angiotech Pharmaceuticals, Vancouver Canada), 95 mg each of polycaprolactone-co-methoxypolyethylene glycol (each containing 17 units of ethylene glycol in the MePEG conjugated to either one unit of caprolactone (PCL1) or 5 units (PCL5) were weighed into a 20 ml glass vial and stirred at 50° C. using a spatula for 5 to 10 minutes. The mixture formed a miscible composition in which all the drug was dissolved. The mixture was sucked up into a 1 ml syringe through an 18 gauge needle and allowed to cool to room temperature.

The waxy material could be injected easily through a 21 gauge needle without compromising the integrity of the composition. When 100 µl of the mixture was injected into 5 ml of water and water acidified to pH 1, the mixture slowly dissolved and there was no precipitation of any of the components. The formulation self assembled into micelles.

Example 3

Injection of Micellar Formulation of Paclitaxel Along the Perivascular Margins of the Carotid Artery of A Rat For the Treatment of Restenosis Wistar rats weighing 400 g to 500 g were anesthetized with halothane. A vertical incision was made over the trachea and the left external carotid artery was exposed. Connective tissue around the left common carotid artery was left untouched. Two ligatures were placed around the external carotid artery and an arteriotomy was made between them. A 2 French Fogarty balloon was introduced into the external carotid artery and pushed into the left common carotid artery and the balloon was inflated with saline. The balloon was passed up and down the entire length of the carotid artery three times to stretch the vessel and denude the endothelium. The balloon was removed and the ligatures tied off on the external carotid artery. A 3% paclitaxel loaded self-assembling micellar composition based on poly-L-lactic acid-MePEG blended with MePEG 350 in a 60/40 weight ratio (as described in Example 2A) was injected through a 24 G angiocatheter between a distal segment of the common carotid artery and the surrounding connective tissue. Typically, 0.1 to 0.2 ml of paste was applied around the artery in 4 injections in order to cover the whole circumference of the vessel on a length of approximately 1 cm. The wound was then closed and the animals recovered.

Using this method various doses of a polymeric dosage form of the antirestenosis compound paclitaxel was applied to the perivascular side of the damaged artery without the need for complete exposure of the artery (as in required for the application of a polymeric film to the artery). The rats tolerated this method of application well with no adverse effects noted in any animal. This example demonstrates a non-invasive method of applying a self assembly micellar formulation of paclitaxel. In this particular example some invasive surgery was used to apply the balloon catheter. However in humans the catheter would be applied from a distant location and it is envisaged that the paste would be applied to the damaged artery in humans via an angiocatheter without surgical exposure of the damaged artery. There was no evidence of toxicity from this method of injection and no sign of drug precipitation at the site of injection along the artery. At the end of two weeks the animals were examined for the presence of residual formulation or local toxicity indicative of non-biocompatible. In all animals treated there was no residual formulation at the site or any evidence of any toxicity in the animals. Clearly, the drug and polymer composition were dissolving and self assembling into a micellar formulation of the drug at the in vivo arterial site.

Example 4

Manufacture of A 10% Paclitaxel Loaded-Self Assembling Micellar Formulation of Paclitaxel Forty mg of paclitaxel (Hauser chemicals), 108 mg of methoxypolyethylene glycol (MePEG) (molecular weight 350) (Union Carbide Inc.) and 252 mg of poly-L-lactic acid-MePEG diblock copolymer (Angiotech Pharmaceuticals, Inc. Vancouver Canada) were weighed into a 20 ml glass vial and stirred at 50° C. using a spatula. The mixture formed a miscible composition in which all the drug was dissolved. The mixture was sucked up into a 1 ml syringe through an 18 gauge needle and allowed to cool to room temperature.

The waxy material could be injected easily through a 21 gauge needle without compromise of the integrity of the composition. When 100 µl of the mixture was injected into 5 ml of water the mixture slowly dissolved. There was no precipitation of any of the components. The formulation self assembled into micelles.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

We claim:

1. A micelle-forming composition comprising:
   (a) a hydrophobic drug;
   (b) a biocompatible block copolymer; and,
   (c) a biocompatible, water soluble polymer,
   wherein, the biocompatible block copolymer includes a hydrophilic portion and a hydrophobic portion, the hydrophilic portion comprising a polyethylene oxide and the hydrophobic portion comprising a polyester, and wherein the water soluble polymer is present in an amount sufficient that the micelle-forming composition is injectable.

2. The composition of claim 1, wherein the composition is substantially free of non-polymeric organic solvent.

3. The composition of claim 1, wherein the polyester of the hydrophobic portion is selected from a group consisting of: polyglycolic acid, polybutrylactone, polyhydroxybutyrate, polylactic acid and polycaprolactone.

4. The composition of claim 3, wherein the polyester has a molecular weight of about 200 to 5000.

5. The composition of claim 1, wherein the polyethylene oxide of the hydrophilic portion is selected from the group consisting of polyethylene glycol (PEG) and methoxypolyethylene glycol (MePEG).

6. The composition of claim 1, wherein the polyethylene oxide has a molecular weight of at least 750.

7. The composition of claim 6, wherein the molecular weight is less than about 8000.

8. The composition of claim 6, wherein the molecular weight is from about 1000 to about 5000.

9. The composition of claim 6, wherein the molecular weight is from about 1000 to about 3000.

10. The composition of claim 6, wherein the molecular weight is from about 1000 to about 2000.

11. The composition of claim 6, wherein the molecular weight is about 2000.

12. The composition of claim 1, wherein the water soluble polymer is polyethylene oxide, wherein the water soluble polymer is a liquid or semi-solid at room temperature.

13. The composition of claim 12, wherein the water soluble polymer is a polyethylene oxide.

14. The composition of claim 13, wherein the polyethylene oxide is selected from the group consisting of PEG and MePEG.

15. The composition of claim 13, wherein the polyethylene oxide has a molecular weight of about 1000 or less.

16. A device for injection of a substance into the body of a patient wherein the device comprises a composition of claim 1 for injection.

17. The device of claim 16, wherein the device is a syringe.

18. The device of claim 17, wherein the syringe further comprises a needle cannula.

19. A method of forming micelles having a hydrophobic drug comprising placing a composition according to claim 1 into an aqueous media.

20. The method of claim 19, wherein said placing is by injection into a site in a patient's body and micelles are formed at the site.

21. A method of using a composition according to claim 1 for administration to a patient comprising forming hydrophobic drug containing micelles within the body of the patient.

22. The method of claim 21, wherein the administration is by injection to a site within the patient's body and the micelles form at the site.

23. A micelle-forming composition comprising:
(a) one or more hydrophobic drugs;
(b) one or more biocompatible, micelle-forming polymers, and,
(c) one or more biocompatible, low molecular weight, water soluble polymers,
wherein the micelle-forming polymer is a block copolymer comprising a hydrophobic and a hydrophilic portion, the hydrophobic portion comprising a polymer block selected from the group consisting of: a polyester; and, the hydrophilic portion is a polyethylene oxide having a molecular weight of about 750 or more.

24. The composition of claim 23, wherein the hydrophobic portion comprises a polymer block selected from the group consisting of: polyglycolic acid, polybutrylactone, polyhydroxybutrate, polylactic acid and polycaprolactone.

25. The composition of claim 23, wherein the hydrophobic portion is a polymer having a molecular weight of about 200 to about 500.

26. The composition of claim 23, wherein the water soluble polymer is polyethylene oxide, wherein the water soluble polymer is a liquid or semi-solid at room temperature.

27. The composition of claim 26, wherein the water soluble polymer is a polyethylene oxide having a molecular weight of 1000 or less selected from the group consisting of PEG and MePEG.

28. The composition of claim 23, wherein the amount of water soluble polymer in the composition is sufficient for the composition to be injectable.

29. The composition of claim 23, wherein the composition is substantially free of organic solvent.

30. The composition according to claim 23, wherein the composition is capable of forming micelles in aqueous medium at a critical micelle concentration(CMC) of about 500 µM or less.

31. The composition according to claim 30, wherein the CMC is about 100 µM or less.

32. The composition according to claim 30, wherein the CMC is about 50 µM or less.

33. A method of forming micelles including a hydrophobic drug, comprising placing a composition according to claim 23 in an aqueous media whereby micelles comprising the hydrophobic drug are formed therein.

34. The method of claim 33, wherein said placing is in vitro.

35. The method of claim 33, wherein said placing is in vivo.

36. A method of using a composition according to claim 23, comprising forming hydrophobic drug containing micelles in vivo.

37. The composition of claim 1 wherein the hydrophobic drug is paclitaxel.

* * * * *